US010153856B2

(12) United States Patent
Xie et al.

(10) Patent No.: US 10,153,856 B2
(45) Date of Patent: Dec. 11, 2018

(54) CHANNEL MULTIPLEXING METHOD FOR READING OUT DETECTOR SIGNAL

(71) Applicant: RAYCAN TECHNOLOGY CO., LTD. (SUZHOU), Suzhou, Jiangsu (CN)

(72) Inventors: Qingguo Xie, Jiangsu (CN); Yuexuan Hua, Jiangsu (CN); Huihua Wen, Jiangsu (CN); Daoming Xi, Jiangsu (CN)

(73) Assignee: RAYCAN TECHNOLOGY CO., LTD. (SUZHOU), Suzhou, Jiangsu (CN)

( * ) Notice: Subject to any disclaimer, the term of this patent is extended or adjusted under 35 U.S.C. 154(b) by 0 days.

(21) Appl. No.: 15/575,634

(22) PCT Filed: May 26, 2016

(86) PCT No.: PCT/CN2016/083418
§ 371 (c)(1),
(2) Date: Nov. 20, 2017

(87) PCT Pub. No.: WO2017/000711
PCT Pub. Date: Jan. 5, 2017

(65) Prior Publication Data
US 2018/0175956 A1    Jun. 21, 2018

(30) Foreign Application Priority Data
Jun. 29, 2015    (CN) .......................... 2015 1 0367105

(51) Int. Cl.
*A61B 6/00*    (2006.01)
*H04J 3/06*    (2006.01)
(Continued)

(52) U.S. Cl.
CPC ............ *H04J 3/0617* (2013.01); *G01T 1/161* (2013.01); *G01T 1/1642* (2013.01);
(Continued)

(58) Field of Classification Search
CPC .... H04J 3/0617; G01T 1/1642; G01T 1/1648; G01T 1/1647; A61B 6/037
See application file for complete search history.

(56) References Cited

U.S. PATENT DOCUMENTS

| 5,187,357 A | 2/1993 | Watanabe |
| 5,198,673 A | 3/1993 | Rougeot et al. |

(Continued)

FOREIGN PATENT DOCUMENTS

| CN | 1438713 A | 8/2003 |
| CN | 1495437 A | 5/2004 |

(Continued)

OTHER PUBLICATIONS

Electrical delay line multiplexing for pulsed mode radiation detectors by Ruud Vinke et al.*

(Continued)

*Primary Examiner* — Siu Lee
(74) *Attorney, Agent, or Firm* — Cantor Colburn LLP

(57) ABSTRACT

A channel multiplexing method for reading out a detector signal is provided, including steps: grouping L detectors to form a first source signal and a second source signal; respectively introducing L detector signals into a first signal transmission line including two readout channels A and B and a second signal transmission line including two readout channels C and D, and providing a first signal delay unit and a second signal delay unit on the first signal transmission line and the second signal transmission line; and symboliz- (Continued)

ing source detectors for forming signals according to pulses of the four readout channels A, B, C and D, and obtaining final pulse information.

16 Claims, 5 Drawing Sheets

(51) Int. Cl.
*G01T 1/161* (2006.01)
*G01T 1/164* (2006.01)
*A61B 6/03* (2006.01)

(52) U.S. Cl.
CPC .......... *G01T 1/1647* (2013.01); *G01T 1/1648* (2013.01); *A61B 6/037* (2013.01)

(56) References Cited

U.S. PATENT DOCUMENTS

| | | |
|---|---|---|
| 7,495,228 B1 | 2/2009 | Albagli et al. |
| 2002/0195563 A1 | 12/2002 | Iida et al. |
| 2003/0063706 A1 | 4/2003 | Ikeda et al. |
| 2004/0056204 A1 | 3/2004 | Tanaka et al. |
| 2007/0036270 A1 | 2/2007 | Okamura et al. |
| 2007/0114423 A1 | 5/2007 | Vester |
| 2008/0083876 A1 | 4/2008 | Endo et al. |
| 2008/0185529 A1 | 8/2008 | Alving et al. |
| 2009/0072158 A1 | 3/2009 | Jung et al. |
| 2009/0127467 A1 | 5/2009 | Frach |
| 2009/0140155 A1 | 6/2009 | Yagi et al. |
| 2009/0302202 A1 | 12/2009 | Sato et al. |
| 2010/0277592 A1 | 11/2010 | Yokoyama et al. |
| 2011/0210255 A1 | 9/2011 | Kim et al. |
| 2012/0012753 A1 | 1/2012 | Fujita et al. |
| 2012/0032088 A1 | 2/2012 | Ishii et al. |
| 2012/0154353 A1 | 6/2012 | Mochizuki et al. |
| 2013/0100302 A1 | 4/2013 | Senda et al. |
| 2013/0140568 A1 | 6/2013 | Miyamoto et al. |
| 2013/0161525 A1 | 6/2013 | Okada et al. |
| 2013/0170620 A1 | 7/2013 | Tredwell et al. |
| 2013/0228697 A1 | 9/2013 | Soh et al. |
| 2013/0299678 A1* | 11/2013 | Arishima ................ H04N 5/32 250/208.1 |
| 2013/0342514 A1 | 12/2013 | Yokoyama et al. |
| 2014/0175294 A1 | 6/2014 | Frach |
| 2015/0001399 A1* | 1/2015 | Fries ..................... G01T 1/2985 250/362 |

FOREIGN PATENT DOCUMENTS

| | | |
|---|---|---|
| CN | 1871999 A | 12/2006 |
| CN | 1971652 A | 5/2007 |
| CN | 101137018 A | 3/2008 |
| CN | 101166998 A | 4/2008 |
| CN | 101238392 A | 8/2008 |
| CN | 101393266 A | 3/2009 |
| CN | 101453576 A | 6/2009 |
| CN | 101551462 A | 10/2009 |
| CN | 101604699 A | 12/2009 |
| CN | 101917907 A | 12/2010 |
| CN | 101930077 A | 12/2010 |
| CN | 102053252 A | 5/2011 |
| CN | 102376725 A | 3/2012 |
| CN | 102388602 A | 3/2012 |
| CN | 102569318 A | 7/2012 |
| CN | 103067668 A | 4/2013 |
| CN | 103179352 A | 6/2013 |
| CN | 103517002 A | 1/2014 |
| CN | 103733609 A | 4/2014 |
| CN | 104023643 A | 9/2014 |
| CN | 203965629 U | 11/2014 |
| CN | 105182396 A | 12/2015 |
| EP | 1746442 A1 | 1/2007 |
| JP | H10275906 A | 10/1998 |
| JP | 2000019015 A | 1/2000 |
| WO | 03063396 A1 | 7/2003 |
| WO | 2013018006 A1 | 2/2013 |

OTHER PUBLICATIONS

International Search Report for corresponding Application No. PCT/CN2016/083418; dated Aug. 22, 2016.

Ruud Vinke et al., "Electrical delay line multiplexing for pulsed mode radiation detectors," Physical Medical Biology; Apr. 7, 2015, pp. 2785-2802.

* cited by examiner

CHANNEL MULTIPLEXING METHOD FOR READING OUT DETECTOR SIGNAL

CROSS REFERENCE TO RELATED APPLICATIONS

This is the U.S. national stage of application No. PCT/CN2016/083418, filed on May 26, 2016. Priority under 35 U.S.C. § 119(a) and 35 U.S.C. § 365(b) is claimed from Chinese Patent Application No. 201510367105.5 titled "CHANNEL MULTIPLEXING METHOD FOR READING OUT DIRECTOR SIGNAL", filed Jun. 29, 2015 with the Chinese State Intellectual Property Office, both of which are incorporated herein by reference in their entireties.

TECHNICAL FIELD

The present disclosure relates to the technical field of nuclear detection and nuclear medicine imaging, and particularly to a channel multiplexing method for reading out detector signals.

BACKGROUND

A clinical positron emission tomography (abbreviated as PET below) device includes 30,000 detectors, and thus 30,000 electronic processing channels are needed for directly reading out electrical signals generated by the respective detectors. The large number of the electronic channels results in high cost and huge difficulty in engineering implementation of a whole PET electronics system.

In view of the above, researchers focus on studying and developing channel multiplexing technology for reading out detector signals. An existing mainstream readout channel multiplexing method is to weigh outputted detector signals based on rows and columns through a resistance network and then read out the output signal.

By multiplexing with the resistance network, the number of readout channels for the detectors is reduced, which solves the problem of excessive channels. However, with the resistance network, equivalent resistances of the resistance network for different detectors are different due to different signal access points, which results in a large difference among amplitudes of output signals of the different detectors. In this case, a large dynamic range is required for a back-end readout circuit. Existing processing circuits normally have a limited dynamic range, that is, a small inputted signal will result in a low signal-to-noise ratio, while a large inputted signal will result in a saturation problem.

Accordingly, in view of the above technical problems, it is necessary to provide a channel multiplexing method providing an improved structure for reading out detector signals, to overcome the above shortcomings and effectively solve the problem of an excessive dynamic range of the signals outputted by the detectors with channel multiplexing.

SUMMARY

In view of this, an objective of the present disclosure is to provide a channel multiplexing method for reading out detector signals, to reduce the number of used electronic channels, effectively lower the requirement on the dynamic range of a back-end readout circuit, and lower the requirement on the temporal resolution of the back-end readout circuit.

In order to achieve the above objective, a technical solution as follows is provided according the present disclosure.

A channel multiplexing method for reading out detector signals is provided, which includes:

step S1: grouping signals of L detectors into M groups, where the number of the detectors in each of the groups is at least 2 and at most N, the number of the signals of the detectors in an a-th group is denoted as P(a), $$L = \sum_{a=1}^{M} P(a),$$

the signal of a b-th detector in the a-th group is denoted as Signal(a,b), where M≥2, N≥2, 1≤a≤M, 1≤b≤N;

step S2: dividing the signals of the L detectors in the step S1 into a first source signal and a second source signal;

step S3: providing a first signal transmission line including two readout channels A and B, inputting the signals of the detectors into the first signal transmission line, and providing at least one first signal delay unit between the signals of the detectors on the first signal transmission line;

step S4: providing a second signal transmission line including two readout channels C and D, inputting the signals of the detectors into the second signal transmission line, and providing at least one second signal delay unit between the signals of the detectors on the second signal transmission line; and step S5: symbolizing source detectors which generate the signals and acquiring final pulse information, based on pulses from the four readout channels A, B, C and D.

In the channel multiplexing method for reading out detector signals described above, preferably, in the step S1, the M groups include the same number of the detectors, the same number is denoted as N, where M×N=L, M≥2, N≥2.

In the channel multiplexing method for reading out detector signals described above, preferably, the first signal transmission line and the second signal transmission line are orthogonal to each other, and positions on the transmission lines are determined based on the delay units dividing the transmission line.

In the channel multiplexing method for reading out detector signals described above, preferably, in the step S3 and the step S4, the two groups of the detectors having corresponding spatial positions are connected to the first signal transmission line and the second signal transmission line respectively.

In the channel multiplexing method for reading out detector signals described above, preferably, in the step S3 and the step S4, two readout channels of each of the detectors are connected to the first signal transmission line and the second signal transmission line respectively.

In the channel multiplexing method for reading out detector signals described above, preferably, in the step S3, the first source signals of the detectors in the a-th group serve as a first signal, M first signals are generated in the M groups, the M first signals are inputted into the first signal transmission line, and the at least one first signal delay unit is provided between two adjacent first signals of the M first signals.

In the channel multiplexing method for reading out detector signals described above, preferably, there are multiple first signal delay units, and the at least one of the first signal delay units is provided between any two adjacent first signals of the M first signals.

In the channel multiplexing method for reading out detector signals described above, preferably, in the step S4, the second source signals of the b-th detectors in respective M groups serve as a second signal, and N second signals are generated, the N second signals are inputted into the second signal transmission line, and the at least one delay unit is provided between two adjacent second signals of the N second signals.

In the channel multiplexing method for reading out detector signals described above, preferably, there are multiple second signal delay units, and the at least one of the second signal delay units is provided between every two adjacent second signals of the N second signals.

In the channel multiplexing method for reading out detector signals described above, preferably, in the step S5, arrival times of each of the signals at the four readout channels A, B, C and D is measured, to calculate a time difference between the arrival time of the signal at the readout channels A and B and a time difference between the arrival time of the signal at the readout channels C and D, a row number and a column number of a source of the signal are determined based on the time differences, and the source detector which generates the signal is symbolized using the two time differences.

In the channel multiplexing method for reading out detector signals described above, preferably, in the step S5, a differential pulse between pulses of the readout channels A and B and a differential pulse between pulses of the readout channels C and D are acquired by a subtraction circuit, and pulse widths of the differential pulses are obtained to represent the time difference between the arrival time of the signal at the readout channels A and B and the time difference between the arrival time of the signal at the readout channels C and D.

In the channel multiplexing method for reading out detector signals described above, preferably, in the step S5, a differential pulse between pulses of the readout channels A and B and a differential pulse between pulses of the readout channels C and D are acquired by a subtraction circuit, and amplitudes of the differential pulses are obtained to represent the time difference between the arrival time of the signal at the readout channels A and B and the time difference between the arrival time of the signal at the readout channels C and D.

In the channel multiplexing method for reading out detector signals described above, preferably, in the step S5, the time difference between the arrival time of the signal at the readout channels A and B is denoted as x, the time difference between the arrival time of the signal at the readout channels C and D is denoted as y, a probability distribution function g(x,y) is calculated, and positions corresponding to the L detectors on the g(x,y) are calculated based on a circuit structure, and separation lines between the adjacent detectors on the g(x,y) are calculate, to distinguish distribution regions corresponding to different detectors on the g(x,y).

In the above channel multiplexing method for reading out detector signals described above, preferably, in the step S5, the time difference between the arrival time of the signal at the readout channels A and B is denoted as x, the time difference between the arrival time of the signal at the readout channels C and D is denoted as y, a probability distribution function g(x,y) is calculated, positions corresponding to the L detectors on the g(x,y) are calculated according to the probability distribution function g(x,y), and separation lines between the adjacent detectors on the g(x,y) are calculated to distinguish distribution regions corresponding to different detectors on the g(x,y).

In the channel multiplexing method for reading out detector signals described above, preferably, in the step S5, the time difference between the arrival time of the signal at the readout channels A and B is denoted as x, the time difference between the arrival time of the signal at the readout channels C and D is denoted as y, a probability distribution function g(x,y) is calculated, positions corresponding to the L detectors on the g(x,y) are calculated based on a circuit structure, and a certain region around each of the positions is set as a distribution region of the detector corresponding to the position on the g(x,y).

In the channel multiplexing method for reading out detector signals described above, preferably, in the step S5, the time difference between the arrival time of the signal at the readout channels A and B is denoted as x, the time difference between the arrival time of the signal at the readout channels C and D is denoted as y, a probability distribution function g(x,y) is calculated, positions corresponding to the L detectors on the g(x,y) are calculated according to the probability distribution function g(x,y), and a certain region around the position is set as a distribution region of the detector corresponding to the position on the g(x,y).

The above technical solution has following advantages compared with conventional technology.

1. The channel multiplexing method for reading out detector signals includes:

step S1: grouping signals of L detectors into M groups, where the number of the detectors in each of the groups is at least 2 and at most N, the number of the signals of the detectors in an a-th group is denoted as P(a), $$L = \sum_{a=1}^{M} P(a),$$

the signal of a b-th detector in the a-th group is denoted as Signal(a,b), where M≥2, N≥2, 1≤a≤M, 1≤b≤N; step S2: dividing the signals of the L detectors in the step S1 into a first source signal and a second source signal; step S3: providing a first signal transmission line including two readout channels A and B, inputting the signals of the detectors into the first signal transmission line, and providing at least one first signal delay unit between the signals of the detectors on the first signal transmission line; step S4: providing a second signal transmission line including two readout channels C and D, inputting the signals of the detectors into the second signal transmission line, and providing at least one second signal delay unit between the signals of the detectors on the second signal transmission line; and step S5: symbolizing source detectors which generate the signals and acquiring final pulse information, based on pulses from the four readout channels A, B, C and D. In the present disclosure, the number of the used electronic channels is reduced, thereby reducing the cost and difficulty of engineering implementation of a whole PET system. Also, it is ensured with time division multiplexing design for the transmission lines that waveforms of signals outputted by detectors at different positions are similar to waveforms read out in a one-to-one manner, thereby lowering the requirement on the dynamic range of a back-end readout circuit. Furthermore, the requirement on the temporal resolution of the back-end readout circuit is greatly lowered by adding the delay unit.

2. In step S1, the M groups include the same number of the detectors, the same number is denoted as N, where M×N=L, M≥2, N≥2. In the technical solution, the number of the detectors in respective rows may be the same with each other or different from each other, which does not affect the method, and depends on practical situations.

3. The first signal transmission line and the second signal transmission line are orthogonal to each other, and positions on the transmission lines are determined based on the delay units dividing the transmission line. In the technical solution, a signal is inputted into the two orthogonal transmission lines, and a position of the detector which outputs the signal is determined based on determined position ranges on the two transmission lines. An output of a plane array detector is acquired through the four readout channels.

4. Two groups of the detectors having corresponding spatial positions are connected to the first signal transmission line and the second signal transmission line respectively, or two readout channels of each detector are connected to the first signal transmission line and the second signal transmission line respectively. In the technical solution, two manners of connecting the detectors to the transmission lines are provided, and a suitable manner may be selected based on practical situations of the detectors. For example, if the detector includes two readout channels, the manner of connecting the two readout channels to the transmission lines may be selected.

5. In step S3, the first source signals of the detectors in the a-th group serve as a first signal, and M first signals are generated in the M groups, the M first signals are inputted into the first signal transmission line, and the at least one first signal delay unit is provided between two adjacent first signals of the M first signals. In the technical solution, the requirement on the temporal resolution of a back-end readout circuit is greatly lowered by adding the delay unit.

6. There are multiple first signal delay units, and at least one of the first signal delay units is provided between any two adjacent first signals of the M first signals. In the technical solution, the delay unit is added for each of the first signals, which facilitates calculation for the time difference.

7. In step S4, the second source signals of the b-th detectors in respective M groups serve as a second signal, and N second signals are generated, the N second signals are inputted into the second signal transmission line, and the at least one delay unit is provided between two adjacent second signals of the N second signals. In the technical solution, the requirement on the temporal resolution of the back-end readout circuit is greatly lowered by adding the delay unit.

8. There are multiple second signal delay units, and at least one of the second signal delay units is provided between every two adjacent second signals of the N second signals. In the technical solution, the delay unit is added for each of the first signals, which facilitates calculation for the time difference.

9. In step S5, arrival time of each of the signals at the four readout channels A, B, C and D are measured, to calculate a time difference between the arrival time of the signal at the readout channels A and B and a time difference between the arrival time of the signal at the readout channels C and D, and a row number and a column number of a source of the signal are determined based on the time differences, and the source detector which generates the signal is symbolized using on the two time differences. In the technical solution, there are multiple manners of calculating the time differences. If information on four pulses is digitized first, the time differences can be calculated based on the arrival times at the four readout channels. Interference from a following analog circuit can be reduced by digitizing the information on the pulses as early as possible.

10. In step S5, a differential pulse between pulses of the readout channels A and B and a differential pulse between pulses of the readout channels C and D are acquired by a subtraction circuit, and pulse widths of the differential pulses are used to represent the time difference between the arrival time of the signal at the readout channels A and B and the time difference between the arrival time of the signal at the readout channels C and D. In the technical solution, the pulse widths of the differential pulses may be used to represent the time differences. If a pulse is outputted with a certain phase difference, the width of the differential pulse of the pulse can be used to represent the phase difference. The number of channels in the back-end readout circuit can be reduced with the method.

11. In step S5, a differential pulse between pulses of the readout channels A and B and a differential pulse between pulses of the readout channels C and D are acquired by a subtraction circuit, and amplitudes of the differential pulses are used to represent the time difference between the arrival time of the signal at the readout channels A and B and the time difference between the arrival time of the signal at the readout channels C and D. In the technical solution, in a case that a phase and rising edge time of the pulse are suitable, the amplitude of the differential pulse may be used to represent the time difference. Instead of measuring the arrival time, peak detection may be adopted to reduce circuit complexity.

12. In step S5, the time difference between the arrival time of the signal at the readout channels A and B is denoted as x, the time difference between the arrival time of the signal at the readout channels C and D is denoted as y, a probability distribution function g(x,y) is calculated, and positions corresponding to the L detectors on the g(x,y) are calculated based on a circuit structure, and separation lines between the adjacent detectors on the g(x,y) are to distinguish distribution regions corresponding to different detectors on the g(x,y). In the technical solution, by calculating the positions corresponding to the detectors on the probability distribution function based on parameters of the circuit structure, difficulty in a testing process is reduced, improving productivity in mass production.

13. In step S5, the time difference between the arrival time of the signal at the readout channels A and B is denoted as x, the time difference between the arrival time of the signal at the readout channels C and D is denoted as y, a probability distribution function g(x,y) is calculated, positions corresponding to the L detectors on the g(x,y) are calculated according to the probability distribution function g(x,y), and separation lines between the adjacent detectors on the g(x,y) are calculated to distinguish distribution regions corresponding to different detectors on the g(x,y). In the technical solution, the separation line between the positions of the different detectors is used to distinguish the distribution regions corresponding to the detectors on the probability distribution function, which improves detection efficiency of a system. Each event is determined with a position.

14. In step S5, the time difference between the arrival time of the signal at the readout channels A and B is denoted as x, the time difference between the arrival time of the signal at the readout channels C and D is denoted as y, a probability distribution function g(x,y) is calculated, positions corresponding to the L detectors on the g(x,y) are calculated based on a circuit structure, and a certain region around each of the positions is set as a distribution region of the detector corresponding to the position on the g(x,y). In the technical solution, by setting a certain area around a position as a distribution region of a detector corresponding to the position on the probability distribution function, an event which is easy to be recognized in error is eliminated, improving a signal-to-noise ratio.

15. In step S5, the time difference between the arrival time of the signal at the readout channels A and B is denoted as x, the time difference between the arrival time of the signal at the readout channels C and D is denoted as y, a probability distribution function g(x,y) is calculated, positions corresponding to the L detectors on the g(x,y) are calculated according to the probability distribution function the g(x,y), and a certain region around each of the positions is set as a corresponding distribution region of the detector corresponding to the position on the g(x,y). In the technical solution, the probability distribution function is acquired based on existing data. With the method, various distribution parameters in a detector array can be reflected, and thus more accurate positions can be obtained, which is more suitable for the detector array.

BRIEF DESCRIPTION OF THE DRAWINGS

In order to illustrating the technical solution according to the embodiments of the present disclosure or in the conventional technology more clearly, the drawings required in description of the embodiments of the present disclosure or the conventional technology is introduced simply. Apparently, the drawings in the following description are only some embodiments of the present disclosure, and other drawings may be obtained by those skilled in the art based on the drawings without creative efforts.

DETAILED DESCRIPTION OF THE EMBODIMENTS

A channel multiplexing method for reading out detector signals is provided according to the present disclosure, to reduce the number of used electronic channels, and effectively lower the requirement on the dynamic range of a back-end readout circuit, and lower the requirement on the temporal resolution of the back-end readout circuit.

Figure 1:
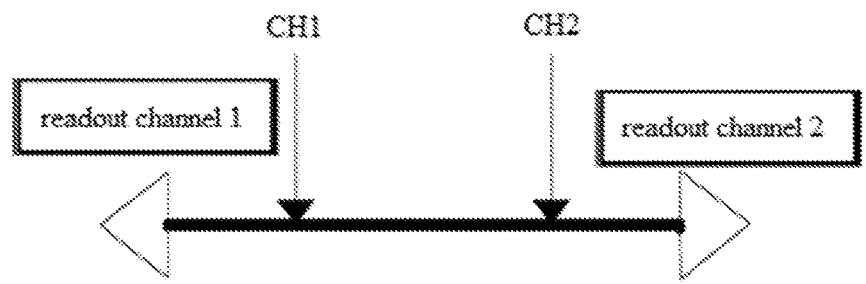
FIG. 1 is a schematic diagram of inputting a pulse signal into a transmission line having readout circuits provided at two ends.
Figure 2:
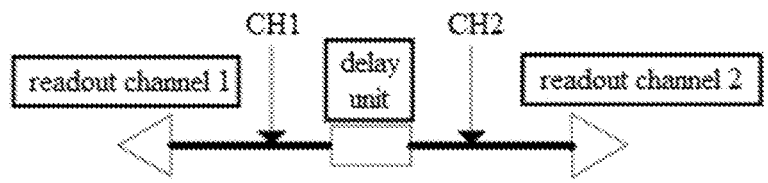
FIG. 2 is a schematic diagram of adding a delay unit on the transmission line in FIG. 1.
Figure 3:
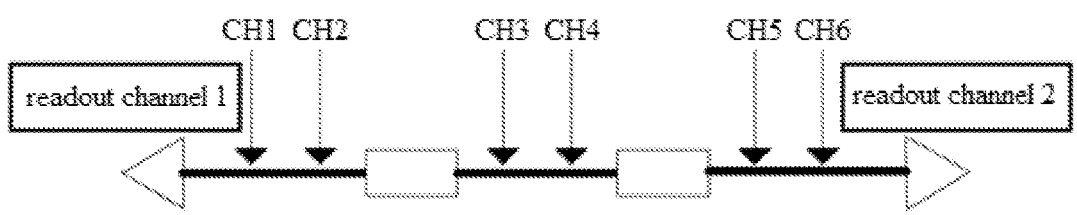
FIG. 3 is a schematic diagram of inputting a pulse signal into a transmission line having readout circuits provided at two ends, and providing multiple delay units on the transmission line.

As shown in FIG. 1, in a case that a pulse signal is inputted into a transmission line having readout circuits provided at two ends, the pulse signal is transmitted toward both ends from an input point. As shown in FIG. 2, one delay unit is added on the transmission line. Since a propagation speed of the signal on the transmission line is much greater than a speed of the signal passing through the delay unit, a time difference between arrival times of the signal at readout channels at the two ends depends on the delay unit on the transmission line. Furthermore, as shown in FIG. 3, several delay units are added on the transmission line. Since a time delay of the delay unit is much greater than a time of transmitting the signal between the input points, the signals inputted into the transmission line may be grouped into multiple groups based on time differences between arrival times of the respective signals at the two ends, that is, a position section (between two adjacent delay units) at which a signal is inputted into the transmission line can be determined by measuring the time difference of the signal. In FIG. 3, the reference number 100 denotes a crystal array, 200 denotes a SIPM detector circuit board 1, and 300 denotes an SIPM detector circuit board 2.

Figure 4:
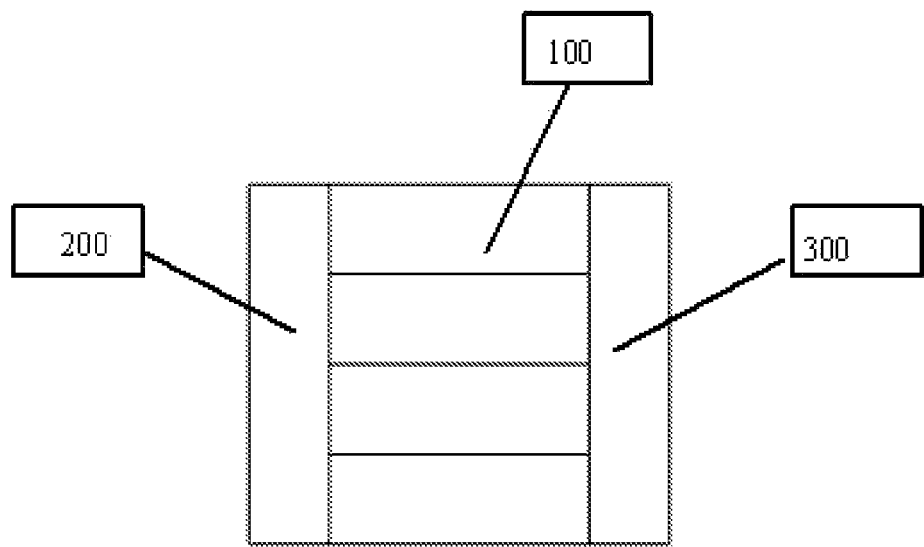
FIG. 4 is a schematic diagram showing a laminated structure of a detector.

The above prototype is applied to the PET detectors. There are multiple types of detectors, such as a silicon photomultiplier (abbreviated as SiPM) detector. The SiPM detector includes a silicon photomultiplier (abbreviated as SiPM) circuit board and a crystal array coupled on the SiPM circuit board. A laminated structure of the detector is as shown in FIG. 4.

Figure 5:
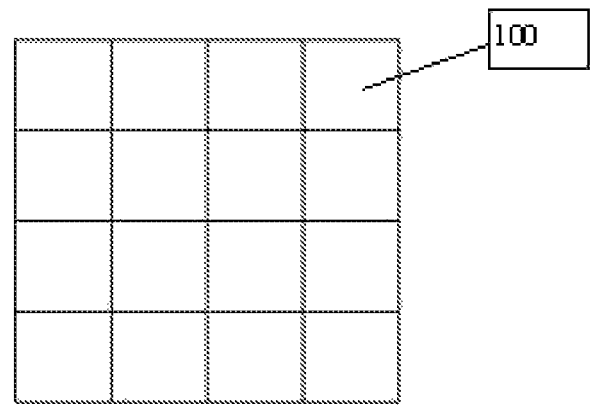
FIG. 5 is a schematic diagram showing a crystal array with a plane array of 4×4.

FIG. 5 is a schematic diagram showing a crystal array with a plane array of 4×4. The technical solution according to the present disclosure is described by taking the crystal array as an example.

Figure 6:
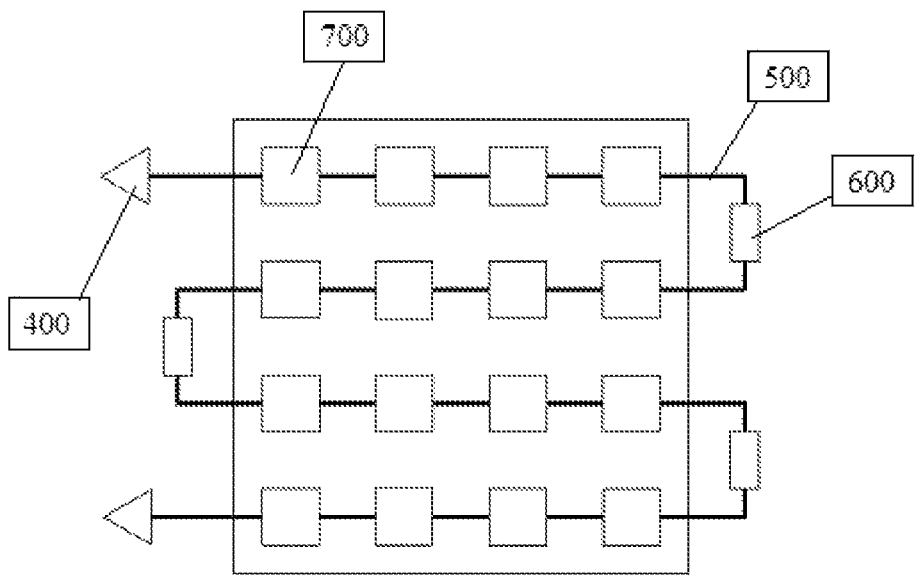
FIG. 6 is a schematic arrangement diagram of a first signal transmission line on a detector circuit board in a channel multiplexing method for reading out detector signals according to the present disclosure.
Figure 7:
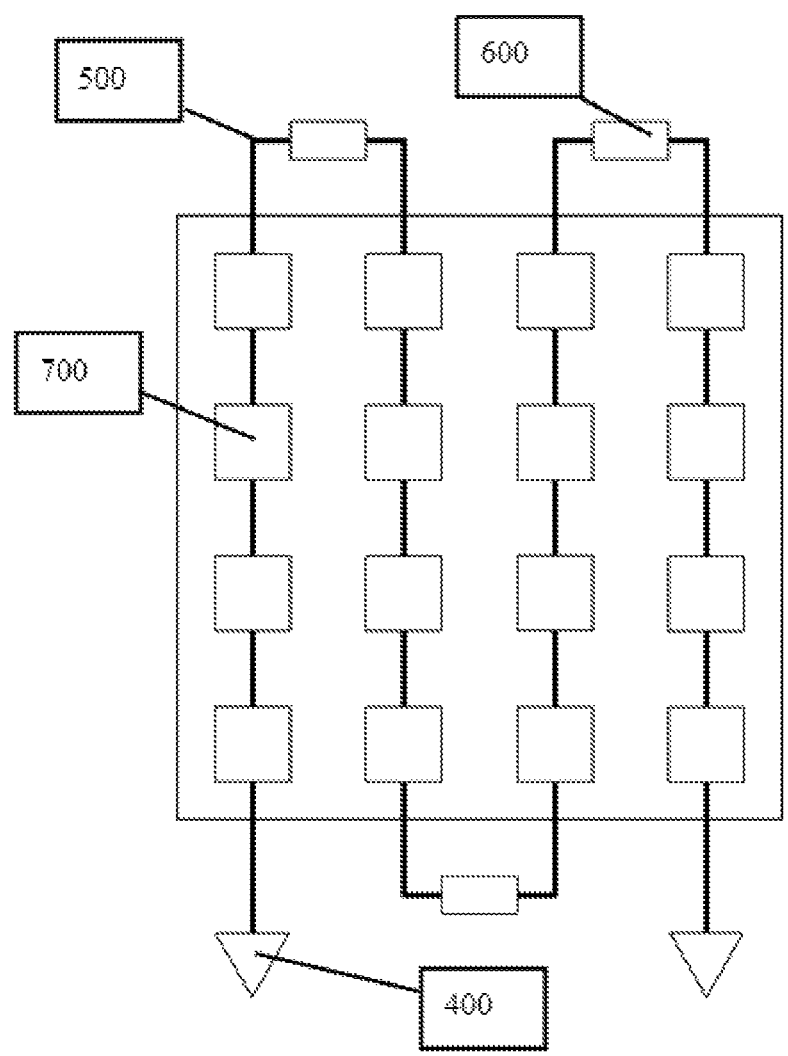
FIG. 7 is a schematic arrangement diagram of a second signal transmission line on a detector circuit board in a channel multiplexing method for reading out detector signals according to the present disclosure.
Figure 8:
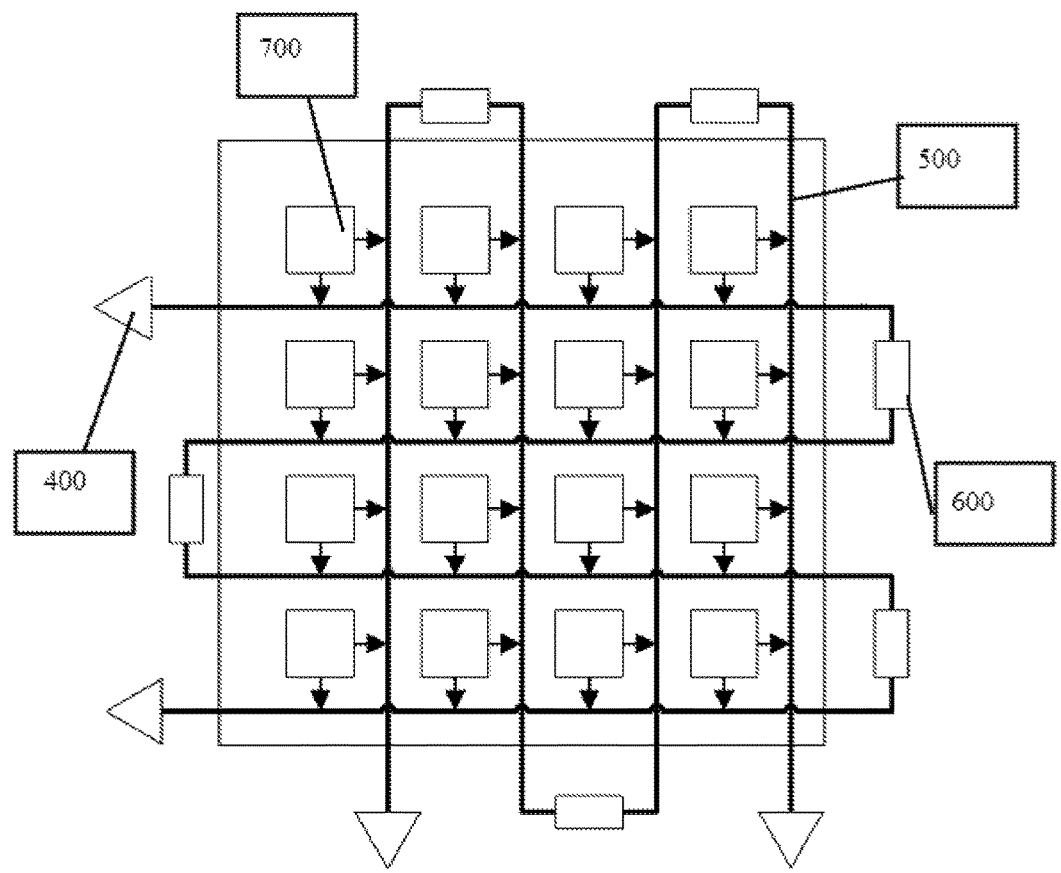
FIG. 8 is a schematic diagram showing that a first signal transmission line is orthogonal to a second signal transmission line in a channel multiplexing method for reading out detector signals according to the present disclosure.

As shown in FIG. 6 to FIG. 8, reference number 400 denotes a readout channel, 500 denotes a transmission line, 600 denotes a delay unit, and 700 denotes the SIPM. A channel multiplexing method for reading out detector signals according to the present disclosure includes step S1 to step S5.

In step S1, signals of L detectors are grouped into M groups. The number of the detectors in each of the groups is at least 2 and at most N, the number of the signals of the detectors in an a-th group is denoted as P(a), $$L = \sum_{a=1}^{M} P(a),$$

the signal of a b-th detector in the a-th group is denoted as Signal(a,b), where M≥2, N≥2, 1≤a≤M, 1≤b≤N;

In step S2, the signals of the L detectors in the step S1 is divided into a first source signal and a second source signal;

In step S3, a first signal transmission line including two readout channels A and B is provided, the signals of the detectors are inputted into the first signal transmission line, and at least one first signal delay unit is provided between the signals of the detectors on the first signal transmission line.

In step S4, a second signal transmission line including two readout channels C and D is provided, the signals of the detectors are inputted into the second signal transmission line, and at least one second signal delay unit is provided between the signals of the detectors on the second signal transmission line.

In step S5, source detectors which generate the signals are symbolized and final pulse information is acquired based on pulses from the four readout channels A, B, C and D.

In the present disclosure, the number of used electronic channels is reduced, thereby reducing the cost and difficulty of engineering implementation of a whole PET system. Also, it is ensured with the time division multiplexing design for the transmission lines that waveforms of signals outputted by detectors at different positions are similar to waveforms read out in a one-to-one manner, thereby lowering the requirement on the dynamic range of a back-end readout circuit. Furthermore, the requirement on the temporal resolution of the back-end readout circuit is greatly lowered by adding the delay unit.

In step S1, the M groups may include the same or different number of detectors. If the M groups include the same number of detectors, the same number may be denoted as N, where M×N=L, M≥2, N≥2. The number of the detectors in respective rows may be the same with each other or different from each other, which does not affect the method, and depends on practical situations.

The first signal transmission line and the second signal transmission line are orthogonal to each other, and the positions on the transmission lines are determined based on the delay units dividing the transmission line. In step S3 and step S4, two groups of the detectors having corresponding spatial positions are connected to the first signal transmission line and the second signal transmission line respectively. Alternatively, two readout channels of each detector are connected to the first signal transmission line and the second signal transmission line respectively. In this way, two orthogonal transmission lines (which may be named as a row transmission line and a column transmission line in a case that the two transmission lines are orthogonal and perpendicular to each other) are provided, and positions (the group of detectors) on the transmission lines are determined based on the delay units dividing the transmission line. Two groups of detectors having corresponding spatial positions may be connected to the two transmission lines respectively, or two readout channels of each detector may be connected to the two transmission lines respectively (in this case, two readout signals can also be considered as signals having corresponding spatial positions). In the technical solution, each signal is inputted into the two orthogonal transmission lines, a position of the detector which outputs the signal is determined based on a determined position range on the two transmission lines, and an output of the plane array detector is acquired through the four readout channels.

The detector may be a SiPM detector, a photodiode detector or any other detector having only one output channel. Two processes may be adopted for a detector having only one output channel, such as a photomultiplier tube (PMT). In the process a, two groups of the detectors having corresponding spatial positions are connected to the two transmission lines respectively. In the process b, each output signal is divided into two signals through an analog circuit, and the two signals are inputted into the two transmission lines respectively. For a detector having two output channels, such as a silicon photomultiplier (abbreviated as SiPM) detector, each signal may be read out simultaneously from two channels, which are an anode and a cathode. When SiPMs are arranged in rows and columns, each signal can be outputted from the anode and the cathode, to form two signals. That is to say, the first source signal and the second source signal may be outputted from the same detector, or may be outputted from two detectors having corresponding spatial positions.

In step S3, the first source signals of the detectors in the a-th group serve as a first signal, and M first signals are formed from the M groups. The M first signals are inputted into the first signal transmission line. At least one first signal delay unit is provided between two adjacent first signals of the M first signals. In the technical solution, the requirement on the temporal resolution of the back-end readout circuit is greatly lowered by adding the delay unit.

In step S4, the second source signals of the b-th detectors in respective M groups serve as a second signal, and N second signals are formed. The N second signals are inputted into the second signal transmission line. At least one delay unit is provided between two adjacent second signals of the N second signals. In the technical solution, the requirement on the temporal resolution of the back-end readout circuit is greatly lowered by adding the delay unit.

There may be multiple first signal delay units and multiple second signal delay units, at least one first signal delay unit is provided between any two adjacent first signals of the M first signals, and at least one second signal delay unit is provided between any two adjacent second signals of the N second signals. In the technical solution, the delay unit is added for each first signal, which facilitates calculation for the time difference.

As shown in FIG. 4, when a γ photon is converted into a visible light photon through a scintillating crystal, the visible light photon is detected by detectors at two ends. The transmission lines connected with detector circuits at the two ends are orthogonal to each other, a crystal strip converting the γ photon can be determined through position information of the two transmission lines, that is, an incident position of the γ photon is detected. In addition, information on depth of energy deposition (DOI) can also be acquired by comparing waveforms detected by the two detectors.

Step S5 is implemented by: measuring arrival time of the signal at the four readout channels A, B, C and D, to calculate a time difference between arrival time of the signal at the readout channels A and B, and calculate a time difference between arrival time of the signal at the readout channels C and D; determining a row number and a column number of a source of the signal based on the time differences; and symbolizing the source detector which generates the signal based on the two time differences. In the technical solution, the time differences may be calculated in multiple manners. If the four pulse information is digitized first, the time differences can be calculated based on the arrival times at the four readout channels. Interference from a following analog circuit can be reduced by digitizing the pulses as early as possible.

The manner for acquiring the time differences includes and is not limited to the following two manners.

In a first manner, a differential pulses between pulses of the readout channels A and B and a differential pulse between pulses of the readout channels C and D are acquired by a subtraction circuit, and pulse widths of the differential pulses are used to represent the time difference between the arrival time of the signal at the readout channels A and B and the time difference between the arrival time of the signal at the readout channels C and D. The pulse widths of the differential pulses are used to represent the time differences. If the same pulse is outputted with a certain phase difference, the width of the differential pulse of the pulse can be used to represent the phase difference. The number of channels in the back-end readout circuit can be reduced with the first manner.

In a second manner, in step S5, a differential pulse between pulses of the readout channels A and B and a differential pulse between pulses of the readout channels C and D are acquired by a subtraction circuit, and amplitudes of the differential pulses are used to represent the time difference between the arrival time of the signal at the readout channels A and B and the time difference between the arrival time of the signal at the readout channels C and D. In a case that the phase and a rising edge time of the pulse are suitable, the amplitude of the differential pulse may be used to represent the time difference. Instead of measuring the arrival time, peak detection may be adopted to reduce the circuit complexity.

The determining the row number and the column number of the source of the signal based on the time differences and symbolizing the source detector which generates the signal based on the two time differences are implemented in the following manners.

In a first manner, in step S5, the time difference between the readout channels A and B is denoted as x, the time difference between the readout channels C and D is denoted as y, a probability distribution function g(x,y) is calculated, positions corresponding to the L detectors on the g(x,y) are calculated according to the probability distribution function g(x,y), and separation lines between the adjacent detectors on the g(x,y) are calculated to distinguish distribution regions corresponding to different detectors on the g(x,y). The probability distribution function is taken as a reference for recognizing the positions of the detectors subsequently. The position of the detector can be calculated according to the probability distribution function, and the position corresponding to the detector is "recognized" on the probability distribution function with a certain calculation method (for example, a white speck on a position and a region around the white speck, such as a region in a square, are set as a position corresponding to a detector). When a pulse is detected afterwards, an obtained (x,y) is matched in the probability density graph, to determine the detector from which the pulse comes. The separation line between the positions of the different detectors is used to distinguish the distribution regions corresponding to the detectors on the probability distribution function, thereby improving detection efficiency of a system. Each event is determined with a position.

In a second manner, the time difference between the readout channels A and B is denoted as x, the time difference between the readout channels C and D is denoted as y, a probability distribution function g(x,y) is calculated, positions corresponding to the L detectors on the g(x,y) are calculated based on a circuit structure, and separation lines between the adjacent detectors on the g(x,y) are calculated to distinguish distribution regions corresponding to different detectors on the g(x,y). When a certain detector in a detector array outputs a pulse signal, the signal is detected at the four readout channels, and the two time differences x and y are calculated. A probability density function may be used to recognize the position of the detector. The value (x,y) corresponding to a certain detector in the array can also be acquired based on the circuit structure. A propagation speed of a pulse in the transmission line can be calculated or measured, and keeps constant. Therefore, the time differences (x,y) corresponding to a certain detector can be calculated based on propagation distances of a signal of the certain detector to the two readout channels in a certain transmission line. This time differences (x,y) can also be taken as a reference for acquiring a position of a detector corresponding to a pulse in the following data acquisition. Calibration for position information of the detector can be acquired based on the circuit structure. By calculating the positions corresponding to the detectors on the probability density function based on parameters of the circuit structure, the difficulty in a testing process is reduced, improving productivity in mass production.

In a third manner, in step S5, the time difference between the readout channels A and B is denoted as x, the time difference between the readout channels C and D is denoted as y, a probability distribution function g(x,y) is calculated, positions corresponding to the L detectors on the g(x,y) are calculated based on a circuit structure, and a certain region around the position is set as a distribution region of the corresponding detector on the g(x,y). By setting the certain region around the position as the distribution region of the corresponding detector on the probability distribution function, an event easy to be recognized in error is eliminated, improving a signal-to-noise ratio.

In a fourth manner, in step S5, the time difference between the readout channels A and B is denoted as x, the time difference between the readout channels C and D is denoted as y, a probability distribution function g(x,y) is calculated, positions corresponding to the L detectors on the g(x,y) are calculated according to the probability distribution function g(x,y), and a certain region around the position is set as a distribution region of the corresponding detector on the g(x,y). By obtaining the probability distribution function based on existing data, various distribution parameters in a detector array can be reflected, and thus more accurate positions can be obtained, which is more suitable for the detector array.

In the third manner and the fourth manner described above, "a certain region" is defined as follows.

1. In the probability distribution function, a circle having a radius of R and a center at the determined position of a detector is taken as "a certain region". The regions corresponding to two adjacent detectors do not overlap with each other. R may be determined by performing two-dimensional Gaussian surface fitting on the speck corresponding to the detector, and taking a radius corresponding to a value which is a half of a maximum value of the function of the Gaussian surface fitting as R. R may also be determined in other manner, and the specific value is reasonably determined according to practical situations.

2. In the probability distribution function, a region where the specks corresponding to the position of the detector is greater that a certain value (for example, ⅓ of a maximum value) is taken as "a certain region", and the specific value is reasonably determined according to practical situations.

In a case that the first manner or the second manner are adopted, that is, the separation line is used to distinguish the positions corresponding to different detectors, all information acquired afterwards are classified to a corresponding detector, i.e., to a corresponding position. In the two manners, the detector has a higher sensitivity, that is, none of detected pulses is "wasted".

In the multiplexing method, if time differences of a new detected pulse are highly matched with multiple points (x,y) in the calibrated position information, and it is difficult to determine which point is best matched with the time differences. For example, in determining to which detector the pulse information belongs, the pulse information close to the separation line has a higher possibility of wrongly determining than the pulse information in the middle of the square. For this case, in the third manner and the fourth manner of "setting a certain region around the position as a distribution region of the corresponding detector on the g(x,y)", a pulse having a higher possibility of wrongly determining the position is directly discarded, thereby reducing an error in the position information.

The probability distribution function g(x,y) is not obtained directly, but calculated statistically. A certain amount of data is acquired first. If 10000 pulses are detected, 10000 (x,y) are acquired, and probabilities at a required fine degree or the numbers of the 10000 pairs of (x,y) is counted. For example, the number of time differences of a certain (x,y) is 100, and the number of time differences of another (x,y) is 50, an obtained three-dimensional graph represents the probability density function. That is, the probability density function is obtained by acquiring some data, to obtain calibration for the position information of the detectors.

As described above, the above embodiments are only intended to illustrate the technical solution of the present disclosure, and not to limit the present disclosure. Although the present disclosure is described in detail with reference to the above embodiments, it should be understood by those skilled in the art that, modifications can be made to the technical solution in the above embodiments, or equivalent substitutions can be made to some of the technical features in the technical solution, and the modifications and the substitutions will not make the essence of the technical solution deviate from the spirit and the scope of the technical solution of the embodiments of the present disclosure.

The invention claimed is:

1. A channel multiplexing method for reading out detector signals, comprising:
step S1: grouping signals of L detectors into M groups, wherein the number of the detectors in each of the groups is at least 2 and at most N, the number of the signals of the detectors in an a-th group is denoted as P(a), $$L = \sum_{a=1}^{M} P(a),$$

the signal or a b-th detector in the a-th group is denoted as Signal(a,b), wherein M≥2, N≥2, 1≤a≤M, 1≤b≤N;
step S2: dividing the signals of the L detectors in the step S1 into a first source signal and a second source signal;
step S3: providing a first signal transmission line comprising two readout channels A and B, inputting the signals of the detectors into the first signal transmission line, and providing at least one first signal delay unit between the signals of the detectors on the first signal transmission line;
step S4: providing a second signal transmission line comprising two readout channels C and D, inputting the signals of the detectors into the second signal transmission line, and providing at least one second signal delay unit between the signals of the detectors on the second signal transmission line; and
step S5: symbolizing, source detectors which generate the signals and acquiring final pulse information, based on pulses from the four readout channels A, B, C and D.

2. The channel multiplexing method for reading out detector signals according to claim 1, wherein in the step S1, the M groups comprise the same number of the detectors, the same number is denoted as N, M×N=L, M≥2, N≥2.

3. The channel multiplexing method for reading out detector signals according to claim 1, wherein:
the first signal transmission line and the second signal transmission line are orthogonal to each other, and positions on the transmission lines are determined based on the delay units dividing the transmission lines.

4. The channel multiplexing method for reading out detector signals according to claim 1, wherein in the step S3 and the step S4, two sets of the detectors having corresponding spatial positions are connected to the first signal transmission line and the second signal transmission line respectively.

5. The channel multiplexing method for reading out detector signals according to claim 1, wherein in the step S3 and the step S4, two readout channels of each of the detectors are connected to the first signal transmission line and the second signal transmission line respectively.

6. The channel multiplexing method for reading out detector signals according to claim 1, wherein in the step S3, the first source signals of the detectors in the a-th group serve as a first signal, M first signals are generated in the M groups, the M first signals are inputted into the first signal transmission line, and the at least one first signal delay unit is provided between two adjacent first signals of the M first signals.

7. The channel multiplexing method for reading out detector signals according to claim 6, wherein there are a plurality of the first signal delay units, and at least one of the first signal delay units is provided between any two adjacent first signals of the M first signals.

8. The channel multiplexing method for reading out detector signals according to claim 1, wherein in the step S4, the second source signals of the b-th detectors in the respective M groups serve as a second signal, and N second signals are generated, the N second signals are inputted into the second signal transmission line, and the at least one second signal delay unit is provided between two adjacent second signals of the N second signals.

9. The channel multiplexing method for reading out detector signals according to claim 8, wherein there are a plurality of the second signal delay units, and at least one of the second signal delay units is provided between any two adjacent second signals of the N second signals.

10. The channel multiplexing method for reading out detector signals according to claim 1, wherein the step S5 comprises:
measuring arrival times of each of the signals at the four readout channels A, B, C and D,
calculating a time difference between the arrival time of the signal at the readout channels A and B and a time difference between the arrival time of the signal at the readout channels C and D,
determining a row number and a column number of a source of the signal based on the time differences, and
symbolizing the source detector which generates the signal using the two time differences.

11. The channel multiplexing method for reading out detector signals according to claim 10, wherein the step S5 comprises:
acquiring, by a subtraction circuit, a differential pulse between pulses of the readout channels A and B and a differential pulse between pulses of the readout channels C and D; and
obtaining pulse widths of the differential pulses to represent the time difference between the arrival time of the signal at the readout channels A and B and the time difference between the arrival time of the signal at the readout channels C and D.

12. The channel multiplexing method for reading out detector signals according to claim 10, wherein the step S5 comprises:
acquiring, by a subtraction circuit, a differential pulse between pulses of the readout channels A and B and a differential pulse between pulses of the readout channels C and D; and obtaining amplitudes of the differential pulses to represent the time difference between the arrival time of the signal at the readout channels A and B and the time difference between the arrival time of the signal at the readout channels C and D.

13. The channel multiplexing method for reading out detector signals according to claim 10, wherein the time difference between the arrival time of the signal at the readout channels A and B is denoted as x, the time difference between the arrival time of the signal at the readout channels C and D is denoted as y, and step S5 comprises:
calculating a probability distribution function g(x,y);
calculating positions corresponding to the L detectors on the g(x,y) based on a circuit structure, and
calculating separation lines between adjacent detectors on the g(x,y), to distinguish distribution regions corresponding to different detectors on the g(x,y).

14. The channel multiplexing method for reading out detector signals according to claim 10, wherein the time difference between the arrival time of the signal at the readout channels A and B is denoted as x, the time difference between the arrival time of the signal at the readout channels C and D is denoted as y, and step S5 comprises:
calculating a probability distribution function g(x,y), and
calculating positions corresponding to the L detectors on the g(x,y) according to the probability distribution function g(x,y), and
calculating separation lines between adjacent detectors on the g(x,y), to distinguish distribution regions corresponding to different detectors on the g(x,y).

15. The channel multiplexing method for reading out detector signals according to claim 10, wherein the time difference between the arrival time of the signal at the readout channels A and B is denoted as x, the time difference between the arrival time of the signal at the readout channels C and D is denoted as y, and step S5 comprises:
calculating a probability distribution function g(x,y),
calculating positions corresponding to the L detectors on the g(x,y) are calculated based on a circuit structure, and
setting a certain region around each of the positions as a distribution region of the detector corresponding to the position on the g(x,y).

16. The channel multiplexing method for reading out detector signals according to claim 10, wherein the time difference between the arrival time of the signal at the readout channels A and B is denoted as x, the time difference between the arrival time of the signal at the readout channels C and D is denoted as y, and step S5 comprises:
calculating a probability distribution function g(x,y),
calculating positions corresponding to the L detectors on the g(x,y) according to the probability distribution function g(x,y), and
setting a certain region around each of the positions as a distribution region of the detector corresponding to the position on the g(x,y).

* * * * *